(12) United States Patent
Shia et al.

(10) Patent No.: US 7,705,024 B2
(45) Date of Patent: Apr. 27, 2010

(54) OXADIAZOLE COMPOUNDS

(75) Inventors: Kak-Shan Shia, Taipei (TW); Cheng-ming Chu, Kaohsiung (TW); Jing-po Tsao, Hsinchu (TW); Yu-Sheng Chao, Warren, NJ (US); Jen-shin Song, Taipei (TW)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 12/050,366

(22) Filed: Mar. 18, 2008

(65) Prior Publication Data

US 2008/0255211 A1    Oct. 16, 2008

Related U.S. Application Data

(60) Provisional application No. 60/911,300, filed on Apr. 12, 2007.

(51) Int. Cl.
*A61K 31/4245* (2006.01)
*C07D 271/06* (2006.01)
*C07D 413/14* (2006.01)

(52) U.S. Cl. ...................... 514/364; 548/131
(58) Field of Classification Search ................ 514/364; 548/131
See application file for complete search history.

(56) References Cited

U.S. PATENT DOCUMENTS 5,624,941 A    4/1997 Barth et al.
7,632,852 B2 * 12/2009 Barth et al. .................. 514/364

FOREIGN PATENT DOCUMENTS

| EP | 1 433 788 | 6/2004 |
|---|---|---|
| EP | 1 479 678 | 11/2004 |
| WO | WO 2005/000820 | 4/2005 |
| WO | WO 2006/087480 | 8/2006 |

OTHER PUBLICATIONS

Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Robert B. Layzer, Section Five- Degenerative Diseases of the Nervous System, Cecil Textbook of Medicine, 20th edition (1996), vol. 2, pp. 2050-2057.*
Antonio R. Damasio, Alzheimer's Disease and Related Dementias, Cecil Textbook of Medicine, 20th edition (1996), vol. 2, pp. 1992-1996.*
FDA mulls drugs to slow late-stage Alzheimer's [online], [retrieved on Sep. 23, 2003]. Retrieved from the Internet, URL: http://www.cnn.com/2003/HEALTH/conditions/09/24/alzheimers.drug.ap/index.html.*

* cited by examiner

*Primary Examiner*—Kamal A Saeed
*Assistant Examiner*—Kristin Bianchi
(74) *Attorney, Agent, or Firm*—Occhiuti Rohlicek & Tsao LLP

(57) ABSTRACT

A compound of formula (I):

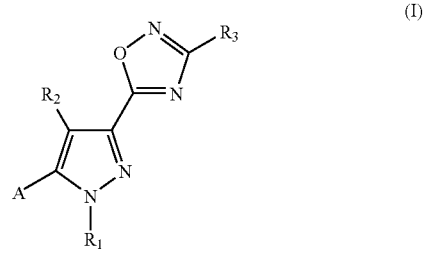

in which A, $R_1$, $R_2$, and $R_3$ are as defined herein. Also disclosed are (1) a pharmaceutical composition containing such a compound, and (2) a method for treating a cannabinoid receptor-mediated disorder using such a compound.

21 Claims, No Drawings

OXADIAZOLE COMPOUNDS

CROSS REFERENCE TO RELATED APPLICATIONS

This application claims priority to U.S. Provisional Application Ser. No. 60/911,300, filed Apr. 12, 2007. The contents of the prior application are hereby incorporated by reference in their entireties.

BACKGROUND

CB1 and CB2 receptors, two subtypes of the cannabinoid receptor, both belong to the G-protein-coupled receptor (GPCR) superfamily.

The CB1 receptor is predominantly expressed in brain to mediate inhibition of transmitter release. It affects many neurological and psychological phenomena, such as mood, appetite, emesis control, memory, spatial coordination muscle tone, and analgesia. See, e.g., Goutopoulos et al., Pharmacol Ther (2002) 95:103.

The CB2 receptor is primarily expressed in immune cells to modulate immune response. Activation of the CB2 receptor has been shown to have analgesic effects in inflammatory models involved in neurodegeneration diseases, and play a role in the maintenance of bone density and progression of atherosclerotic lesions. See, e.g., Malan et al., Pain (2001) 93:239; Benito et al., J Neurosci (2003) 23:11136; Ibrahim et al., Proc Natl Acad Sci USA (2003) 100:10529; Idris et al., Nat Med (2005) 11:774; and Steffens et al., Nature (2005) 434:782.

SUMMARY

The present invention is based on a surprising discovery that a group of oxadiazole compounds effectively bind to the CB1 or CB2 receptor, thereby modulating the activity of the receptor.

Thus, in one aspect, this invention relates to a group of oxadiazole compounds that have the following formula:

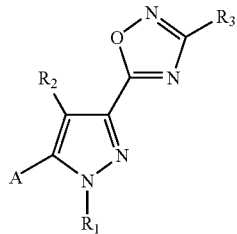

in which each of $R_1$, $R_2$, and $R_3$, independently, is H, halo, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, or heteroaryl; and A is heteroaryl optionally substituted with halo, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, or heteroaryl or optionally fused with a 3-8 membered ring containing 0-3 heteroatoms.

Referring to this formula, the compounds can have one or more of the following features: $R_1$ is aryl substituted with halo (e.g., 2,4-dichlorophenyl); $R_3$ is $C_1$-$C_{10}$ alkyl; and A is 5-membered heteroaryl optionally substituted with halo, $C_1$-$C_{10}$ alkyl, $C_2$-$C_{10}$ alkenyl, or $C_2$-$C_{10}$ alkynyl or optionally fused with a 3-8 membered ring containing 0-3 heteroatoms. Examples of A include, but are not limited to, thienyl substituted with halo (e.g., thien-2-yl substituted with Br), thien-2-yl fused with a 5-7 membered ring containing 0-1 nitrogen atom, selenophenyl substituted with halo (e.g., selenophen-2-yl substituted with Br), selenophenyl fused with a 3-8 membered ring containing 0-3 heteroatoms, and selenophen-2-yl fused with a 5-7 membered ring containing 0 or 1 nitrogen atom.

The term "halo" refers to any radical of fluorine, chlorine, bromine, or iodine.

The term "alkyl" refers to a straight or branched hydrocarbon, containing 1-10 carbon atoms. Examples of alkyl include, but are not limited to, methyl, ethyl, n-propyl, i-propyl, n-butyl, i-butyl, and t-butyl. The term "alkenyl" refers to a straight or branched hydrocarbon containing 2-10 carbon atoms and one or more double bonds. Examples of alkenyl, but are not limited to, include ethenyl, propenyl, allyl, and 1,4-butadienyl. The term "alkynyl" refers to a straight or branched hydrocarbon containing 2-10 carbon atoms and one or more triple bonds. Examples of alkynyl include, but are not limited to, ethynyl, 1-propynyl, 1- and 2-butynyl, and 1-methyl-2-butynyl. The term "alkoxy" refers to an —O-alkyl radical. Examples of alkoxy include, but are not limited to, methoxy, ethoxy, n-propoxy, isopropoxy, n-butoxy, iso-butoxy, sec-butoxy, and tert-butoxy.

The term "cycloalkyl" refers to a saturated hydrocarbon ring system having 3 to 12 carbon atoms. Examples of cycloalkyl include, but are not limited to, cyclopropyl, cyclobutyl, cyclopentyl, cyclohexyl, cycloheptyl, and cyclooctyl. The term "cycloalkenyl" refers to a non-aromatic hydrocarbon ring system having 3 to 12 carbons and one or more double bonds. Examples include cyclopentenyl, cyclohexenyl, and cycloheptenyl. The term "heterocycloalkyl" refers to a nonaromatic 5-8 membered monocyclic, 8-12 membered bicyclic, or 11-14 membered tricyclic ring system having one or more heteroatoms (such as O, N, S, or Se). Examples of heterocyclyl groups include, but are not limited to, piperazinyl, pyrrolidinyl, dioxanyl, morpholinyl, and tetrahydrofuranyl. The term "heterocycloalkenyl" refers to a nonaromatic 5-8 membered monocyclic, 8-12 membered bicyclic, or 11-14 membered tricyclic ring system having one or more heteroatoms (such as O, N, S, or Se) and one or more double bonds.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to an aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, cycloalkenyl, heterocycloalkenyl, aryl, and heteroaryl mentioned herein include both substituted and unsubstituted moieties. Examples of substituents include, but are not limited to, halo, hydroxy, amino, cyano, nitro, mercapto, alkoxycarbonyl, amido, alkanesulfonyl, alkylcarbonyl, carbamido, carbamyl, carboxy, thioureido, thiocyanato, sulfonamido, alkyl, alkenyl, alkynyl, alkyloxy, aryl, heteroaryl, cyclyl, and heterocyclyl.

Shown in the table below are 18 exemplary compounds of this invention:

Compound 8
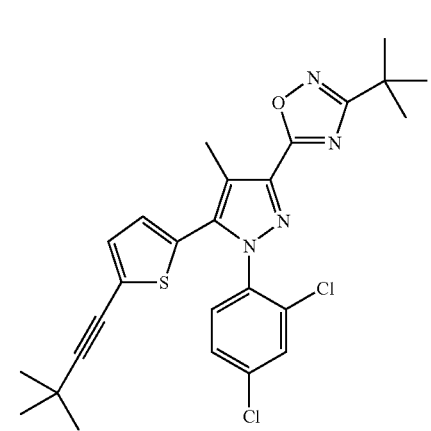
Compound 9
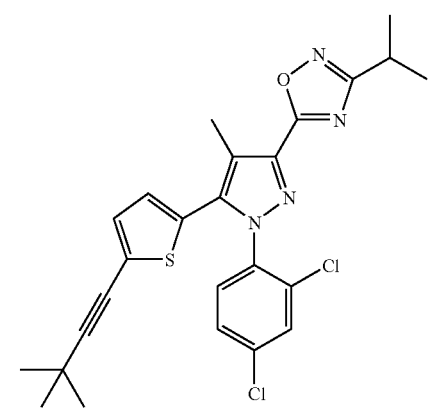
Compound 10
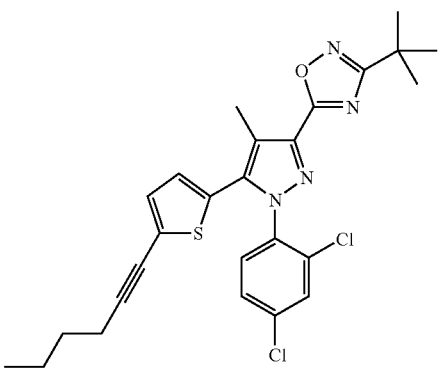
Compound 11
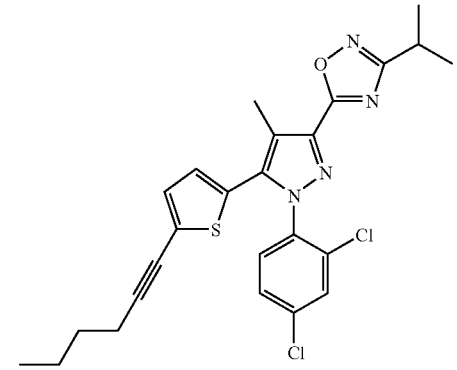
Compound 12
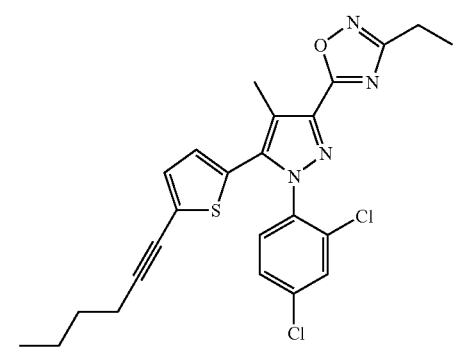
Compound 13
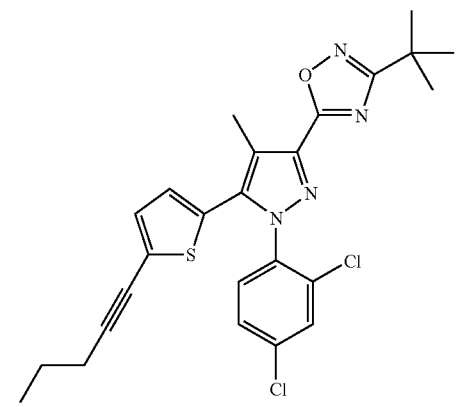
Compound 14
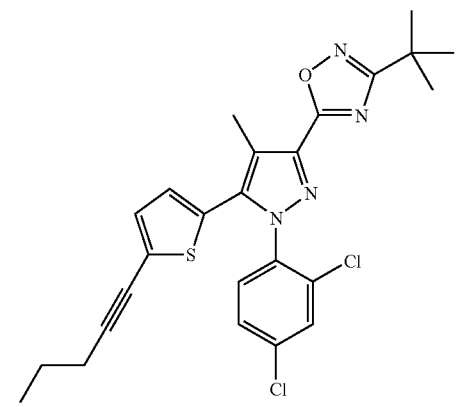

Compound 15
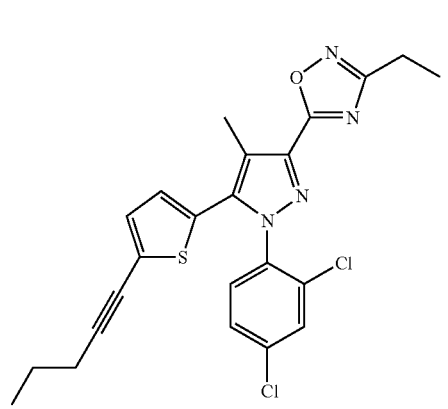

Compound 16
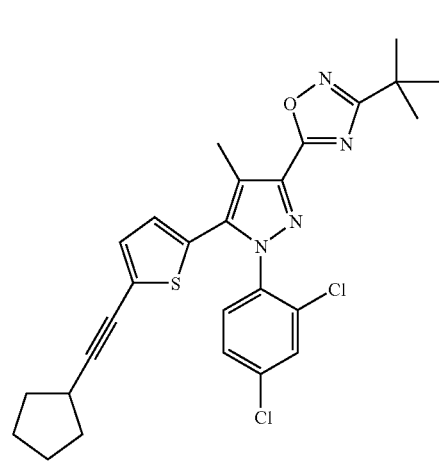

Compound 17
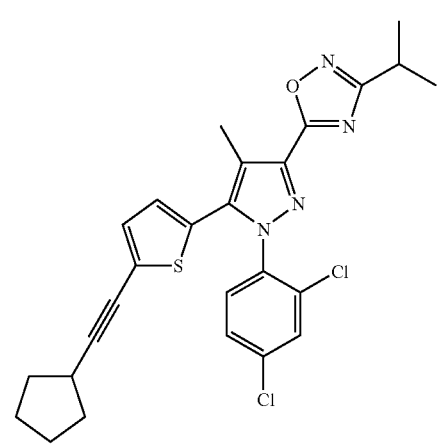

Compound 18
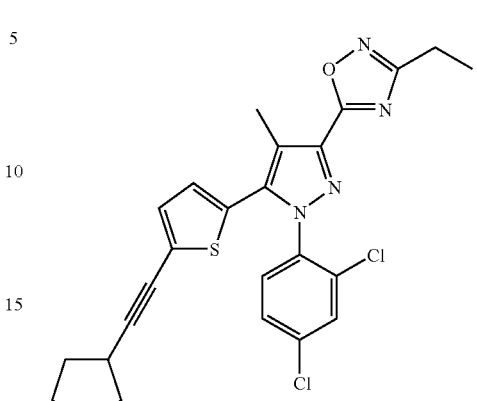

In another aspect, this invention relates to a method of treating a cannabinoid receptor-mediated disorder by administering to a subject in need of this treatment an effective amount of one or more of the compounds described above. Cannabinoid receptor-mediated disorders include, but are not limited to, cancer (e.g., prostate cancer, lung cancer, breast cancer, or head and neck cancer), metabolic syndrome, obesity, hyperlipidemia, type II diabetes, atherosclerosis, substance addition, liver cirrhosis, schizophrenia, sexual dysfunction, anxiety, depression, motivational deficiency syndrome, learning or memory dysfunction, analgesia, haemorrhagic shock, ischemia, neuropathic pain, antiemesis, hair loss, high intraocular pressure, bronchodilation, osteoporosis, neurodegenerative diseases, or inflammatory diseases.

Also within the scope of this invention is a pharmaceutical composition containing one or more of the oxadiazole compounds for use in treating a cannabinoid receptor-mediated disorder, as well as this use and use of the compound for the manufacture of a medicament for treating a cannabinoid receptor-mediated disorder.

The details of one or more embodiments of the invention are set forth in the accompanying drawings and the description below. Other features, objects, and advantages of the invention will be apparent from the description and drawings, and from the claims.

DETAILED DESCRIPTION

The compounds of this invention feature a 5-pyrazol-3-yl-oxadiazole core structure. To synthesize these compounds, one can use synthetic chemistry transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof. Schemes 1-3 below show exemplary methods of synthesizing the compounds of this invention.

Scheme 1

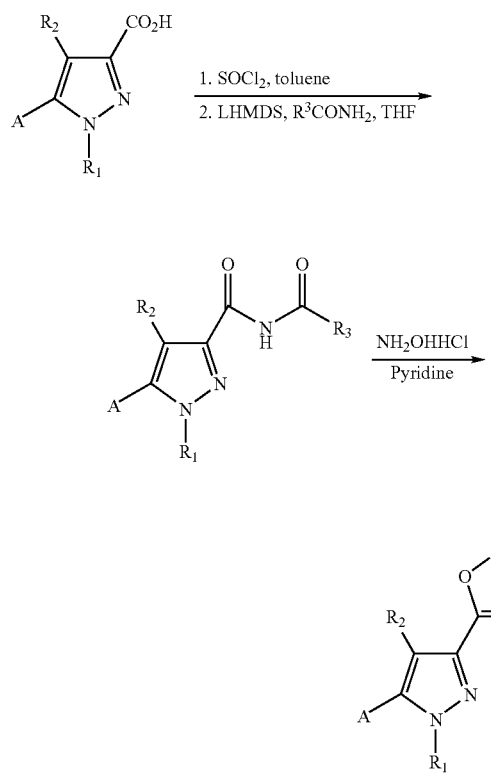

Scheme 1 illustrates a synthetic route to a 5-pyrazol-3-yl-oxadiazole compound from pyrazole-3-carboxylic acid. More specifically, pyrazole-3-carboxylic acid is reacted first with thionyl chloride and then with amide to form N-acyl pyrazole-3-carboxamide, followed by cyclization with hydroxylamine.

Scheme 2

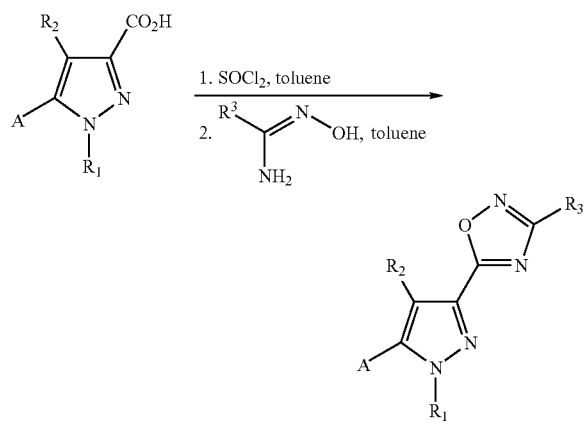

Scheme 2 shows an alternative synthetic route to 5-pyrazol-3-yl-oxadiazole compound, i.e., reacting pyrazole-3-carboxylic acid first with thionyl chloride and then with N'-hydroxy alkylimidamide compound to directly form a 5-pyrazol-3-yl-oxadiazole compound.

Scheme 3

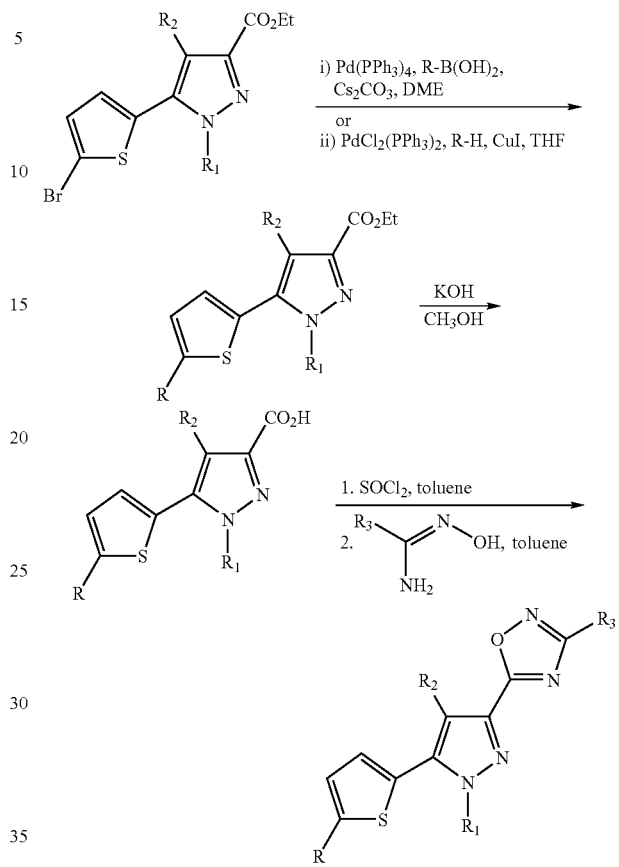

Scheme 3 shows a synthetic route to 5-(5'-thienyl-substituted)pyrazol-3-yl-oxadiazole, in which a 5-thienyl substituted pyrazole carboxylic acid ester is used as a starting material. The substituents on the thienyl group can be introduced by well known coupling reactions, e.g., Suzuki or Sonogashira reaction.

Pyrazole-3-carboxylic acid ester used in the above schemes can be prepared by well-known methods. For example, one can react acetoacetate with a hydrazine compound to form pyrazole-3-carboxylic acid ester.

The oxadiazole compounds thus synthesized can be further purified by flash column chromatography, high performance liquid chromatography, crystallization, or any other suitable methods.

The oxadiazole compounds of this invention are able to modulate the activity of a CB1 or CB2 receptor, e.g., inhibiting or activating the activity. Thus, this invention also relates to a method for treating cannabinoid receptor-mediated diseases. The method can be performed by administering to a subject in need of this treatment an effective amount of one of the oxadiazole compounds.

As used herein, the term "treating" refers to administering an oxadiazole compound to a subject that has a disorder, e.g., a disorder mediated by the CB1 cannabinoid receptor, or has a symptom of such a disorder, or has a predisposition toward such a disorder, with the purpose to cure, heal, alleviate, relieve, alter, remedy, ameliorate, improve, or affect the disorder, the symptoms of the disorder, or the predisposition toward the disorder. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

To practice the method provided in this application, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. An oxadiazole compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form more soluble complexes with the oxadiazole compounds, or more solubilizing agents, can be utilized as pharmaceutical carriers for delivery of the oxadiazole compounds. Examples of other carriers include colloidal silicon dioxide, magnesium stearate, sodium lauryl sulfate, and D&C Yellow #10.

Suitable in vitro assays can be used to preliminarily evaluate the binding affinity of the oxadiazole compounds of this invention to the CB1 or CB2 receptor. The compounds can further be examined for their efficacy in treating a cannabinoid receptor-mediated disease. For example, a compound can be administered to an animal (e.g., a mouse model) having a cannabinoid receptor-mediated disease (e.g., cancer) and its therapeutic effects are then assessed. Based on the results, an appropriate dosage range and administration route can also be determined.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Examples 1-16 describe preparation of intermediates useful for making the oxadiazole compounds of this invention. Examples 17-34 describe preparation of 18 oxzdiazole compounds of this invention. Example 35 describes in vitro assays in which oxazodazole compounds were tested for their binding affinity to, and functional activity towards, a CB1 or CB2 receptor.

Example 1

Preparation of 1-(2,4-dichloro-phenyl)-4-methyl-5-selenophen-2-yl-1H-pyrazole-3-carboxylic acid ethyl ester

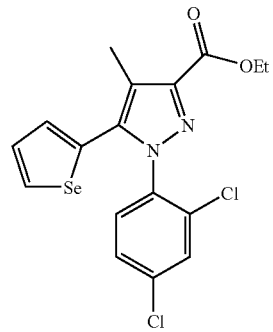

To a solution of lithium bis(trimethylsilyl)amide (17.6 mL, 1.0 M solution in THF 17.64 mmol) in diethyl ether (40 mL) was added under stirring a solution of 1-(selenophene-2-yl)-propan-1-one (3.0 g, 16.0 mmol) in dry diethyl ether (15 mL) at −78° C. After 45 min, diethyl oxalate (2.6 mL, 19.24 mmol) was added. The reaction mixture was allowed to warm to room temperature and then stirred for 16 h. The precipitate was filtered out, washed with dry diethyl ether, and dried under vacuum to afford lithium salt (3.0 g, 65%).

To the above lithium salt (3.0 g, 10.2 mmol) in ethanol (40 mL) was added 2,4-dichlorophenylhydrazine hydrochloride (2.4 g, 11.2 mmol) in one portion at room temperature. The resulting mixture was stirred at room temperature for 20 h. The precipitate was filtered, washed with diethyl ether, and then dried under vacuum to give a light yellow solid (3.2 g, 70%). The solid was dissolved in acetic acid (30 mL) and heated to reflux for 24 h. The reaction mixture was poured into ice water and extracted with ethyl acetate. The combined organic layers were washed with water, saturated aqueous sodium bicarbonate, and brine, dried over anhydrous sodium sulfate, filtered, and evaporated. Purification by flash column chromatography on silica gel with n-hexane/ethyl acetate (9:1) gave the desired ester (2.4 g, 80%) as a white solid.

Example 2

Preparation of 1-(2,4-dichloro-phenyl)-4-methyl-5-thiophen-2-yl-1H-pyrazole-3-carboxylic acid ethyl ester

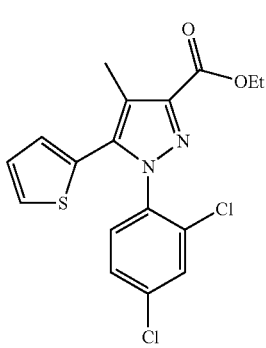

The compound was prepared in a manner similar to that described in Example 1.

Example 3

Preparation of 5-(5-bromo-selenophen-2-yl)-1-(2,4-dichloro-phenyl)-4-methyl-1H-pyrazole-3-carboxylic acid ethyl ester

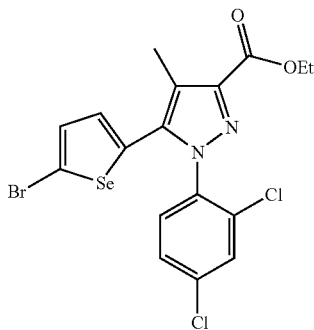

NBS (1.6 g, 9.34 mmol) was added in several small portions to a magnetically stirred solution of 1-(2,4-dichloro-phenyl)-4-methyl-5-selenophen-2-yl-1H-pyrazole-3-carboxylic acid ethyl ester (2.0 g, 4.67 mmol) in acetonitrile at 0° C. The resulting mixture was stirred at room temperature for 48 h. The precipitate was filtered out, washed with saturated aqueous sodium sulfite and cold water, and then dried under vacuum to give the desired compound (2.2 g, 92%) as a white solid.

Example 4

Preparation of 5-(5-bromo-thiophen-2-yl)-1-(2,4-dichloro-phenyl)-4-methyl-1H-pyrazole-3-carboxylic acid ethyl ester

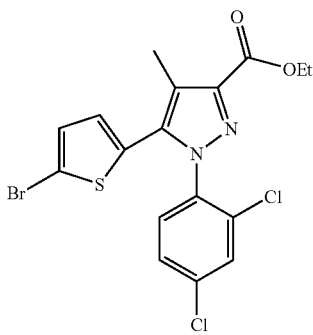

The compound was prepared in a manner similar to that described in Example 3.

Example 5

Preparation of 5-(5-bromo-selenophen-2-yl)-1-(2,4-dichloro-phenyl)-4-methyl-1H-pyrazole-3-carboxylic acid

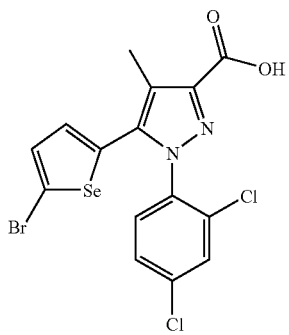

A solution of potassium hydroxide (442 mg, 7.88 mmol) in methanol (7 mL) was added to a magnetically stirred solution of 5-(5-Bromo-selenophen-2-yl)-1-(2,4-dichloro-phenyl)-4-methyl-1H-pyrazole-3-carboxylic acid ethyl ester (2.0 g, 3.94 mmol) in methanol (15 mL). The mixture was heated under reflux for 3 h. The reaction mixture was cooled, poured into water, and acidified with 10% hydrochloric acid. The precipitate was filtered out, washed with water, and dried under vacuum to yield the corresponding acid (1.8 g, 95%) as a white solid.

Example 6

Preparation of 5-(5-bromo-thiophen-2-yl)-1-(2,4-dichloro-phenyl)-4-methyl-1H-pyrazole-3-carboxylic acid

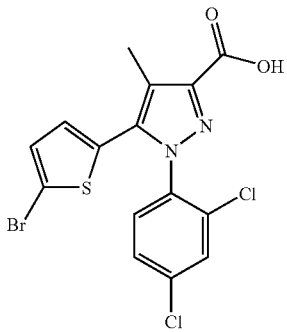

The compound was prepared from 5-(5-Bromo-thiophen-2-yl)-1-(2,4-dichloro-phenyl)-4-methyl-1H-pyrazole-3-carboxylic acid ethyl ester in a manner similar to that described in Example 5.

Example 7

Preparation of 1-(2,4-dichloro-phenyl)-4-methyl-5-[((E)-5-propenyl)-thiophen-2-yl]-1H-pyr-azole-3-carboxylic acid ethyl ester

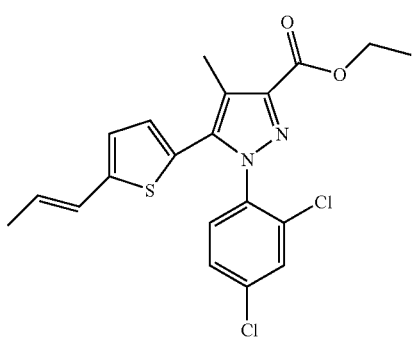

A solution of 5-(5-Bromo-thiophen-2-yl)-1-(2,4-dichloro-phenyl)-4-methyl-1H-pyrazole-3-carboxylic acid ethyl ester (500 mg, 1.09 mmol), (E)-prop-1-enylboronic acid (112 mg, 1.30 mmol), tetrakis-triphenylphosphinopallidum (115 mg, 0.10 mmol), and cesium carbonate (710 mg, 2.18 mmol) in DME (15 mL) was refluxed for 3 h. The precipitate was filtered and washed with ethyl acetate. The solvent was evaporated under reduced pressure, and the resulting residue was purified by flash column chromatography with n-hexane/ethyl acetate (5:1) to give the desired compound (330 mg, 72%) as a light solid.

Example 8

Preparation of 1-(2,4-dichloro-phenyl)-5-[5-(3,3-dimethyl-but-1-ynyl)-thiophen-2-yl]-4-methyl-1H-pyrazole-3-carboxylic acid ethyl ester

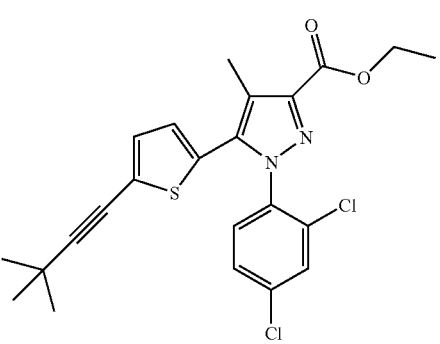

To a suspension of 5-(5-bromo-thiophen-2-yl)-1-(2,4-dichloro-phenyl)-4-methyl-1H-pyrazole-3-carboxylic acid ethyl ester (500 mg, 1.09 mmol), PdCl$_2$(PPh$_3$)$_2$ (23 mg, 0.03 mmol), and CuI (4 mg, 0.01 mmol) in THF (10 mL) was added 4,4-dimethylpent-1-yne (176 mg, 1.30 mmol) and 0.5 M aqueous solution of 2-ethanolamine (3 mL). The resulting mixture was heated at 60° C. for 6 h. After cooled to room temperature, the reaction mixture was poured into water and diethyl ether (H$_2$O/ether=1:1 (v/v), 20 mL). The aqueous layer was extracted with diethyl ether and the combined organic layers were concentrated to give a crude oil, which was purified by flash column chromatography with n-hexane/ethyl acetate (5:1) to afford the desired product (402 mg, 80%) as a light solid.

Example 9

Preparation of 1-(2,4-dichloro-phenyl)-5-(5-hex-1-ynyl-thiophen-2-yl)-4-methyl-1H-pyrazole-3-carboxylic acid ethyl ester

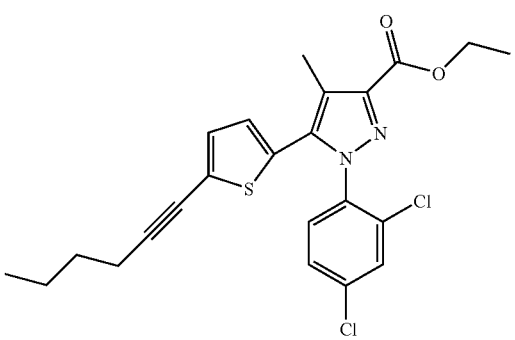

The compound was prepared in a manner similar to that described in Example 8.

Example 10

Preparation of 1-(2,4-dichloro-phenyl)-4-methyl-5-(5-pent-1-ynyl-thiophen-2-yl)-1H-pyrazole-3-carboxylic acid ethyl ester

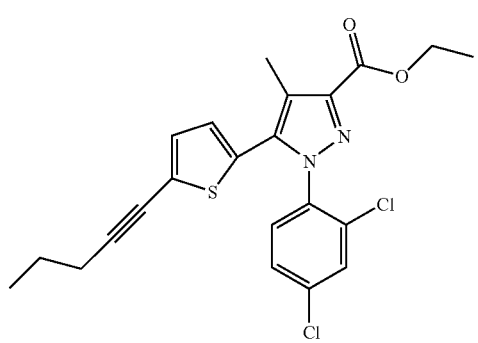

The compound was prepared in a manner similar to that described in Example 8.

Example 11

Preparation of 5-(5-cyclopentylethynyl-thiophen-2-yl)-1-(2,4-dichloro-phenyl)-4-methyl-1H-pyrazole-3-carboxylic acid ethyl ester

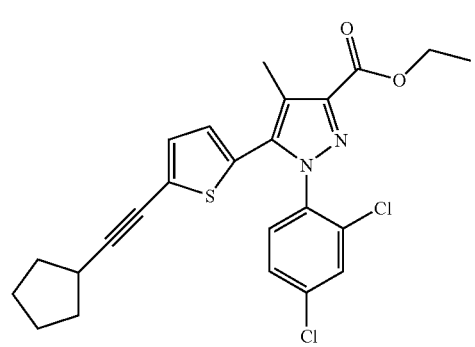

The compound was prepared in a manner similar to that described in Example 8.

Example 12

Preparation of 1-(2,4-dichloro-phenyl)-4-methyl-5-[((E)-5-propenyl)-thiophen-2-yl]-1H-pyrazole-3-carboxylic acid

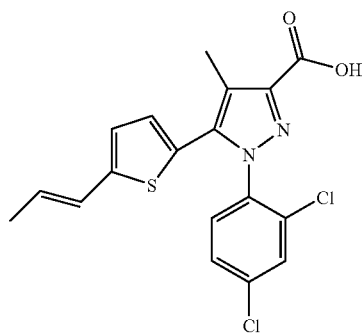

The compound was prepared from 1-(2,4-dichloro-phenyl)-4-methyl-5-[((E)-5-propenyl)-thiophen-2-yl]-1H-pyrazole-3-carboxylic acid ethyl ester in a manner similar to that described in Example 6.

Example 13

Preparation of 1-(2,4-dichloro-phenyl)-5-[5-(3,3-dimethyl-but-1-ynyl)-thiophen-2-yl]-4-methyl-1H-pyrazole-3-carboxylic acid

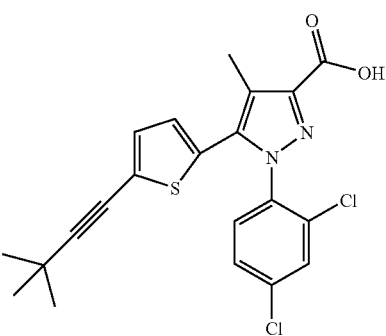

The compound was prepared from 1-(2,4-dichloro-phenyl)-5-[5-(3,3-dimethyl-but-1-ynyl)-thiophen-2-yl]-4-methyl-1H-pyrazole-3-carboxylic acid ethyl ester in a manner similar to that described in Example 6.

Example 14

Preparation of 1-(2,4-dichloro-phenyl)-5-(5-hex-1-ynyl-thiophen-2-yl)-4-methyl-1H-pyrazole-3-carboxylic acid

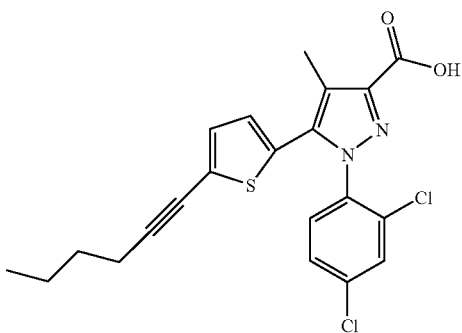

The compound was prepared from 1-(2,4-dichloro-phenyl)-5-(5-hex-1-ynyl-thiophen-2-yl)-4-methyl-1H-pyrazole-3-carboxylic acid ethyl ester in a manner similar to that described in Example 6.

Example 15

Preparation of 1-(2,4-dichloro-phenyl)-4-methyl-5-(5-pent-1-ynyl-thiophen-2-yl)-1H-pyrazole-3-carboxylic acid

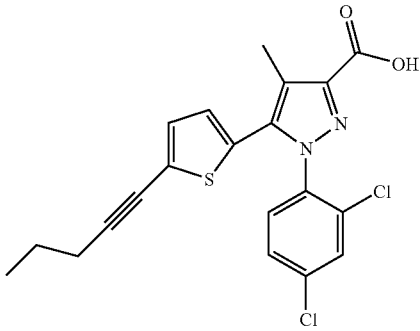

The compound was prepared from 1-(2,4-dichloro-phenyl)-4-methyl-5-(5-pent-1-ynyl-thiophen-2-yl)-1H-pyrazole-3-carboxylic acid ethyl ester in a manner similar to that described in Example 6.

Example 16

Preparation of 5-(5-cyclopentylethynyl-thiophen-2-yl)-1-(2,4-dichloro-phenyl)-4-methyl-1H-pyrazole-3-carboxylic acid

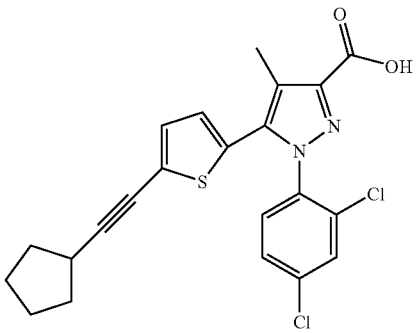

The compound was prepared from 5-(5-cyclopentylethynyl-thiophen-2-yl)-1-(2,4-dichloro-phenyl)-4-methyl-1H-pyrazole-3-carboxylic acid ethyl ester in a manner similar to that described in Example 6.

Example 17

Preparation of 5-(5-(5-bromoselenophen-2-yl)-1-(2,4-dichlorophenyl)-4-methyl-1H-pyrazol-3-yl)-3-tert-butyl-1,2,4-oxadiazole

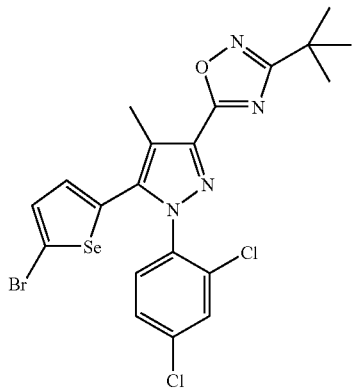

A solution of the acid obtained in Example 5 and thionyl chloride (6 eq.) in toluene was refluxed for 3 h. The solvent was evaporated under reduced pressure, and the crude carboxylic chloride was formed as a light solid (100 mg). The thus-obtained carboxylic chloride, without purification, was dissolved in toluene and allowed to react with N-hydroxypivalimidamide (67 mg) at refluxing temperature for 2 h. After the reaction was cooled and quenched with water, the aqueous layer was separated and extracted with dichloromethane (2×10 mL). The combined organic layers were washed with brine, dried over anhydrous sodium sulfate, filtered, and evaporated. By flash column chromatography of the crude product on silica gel with n-hexane/ethyl acetate (9:1) gave the desired compound (78 mg, 70%) as a white solid.

$^1$H NMR (CDCl$_3$, ppm) 7.49 (d, 1H), 7.40 (s, 1H), 7.37 (d, 1H), 7.19 (d, 1H), 6.89 (d, 1H), 2.52 (s, 3H), 1.45 (s, 9H); ESMS 558.9 (M+1).

Example 18

Preparation of 5-(5-(5-bromoselenophen-2-yl)-1-(2,4-dichlorophenyl)-4-methyl-1H-pyrazol-3-yl)-3-isopropyl-1,2,4-oxadiazole

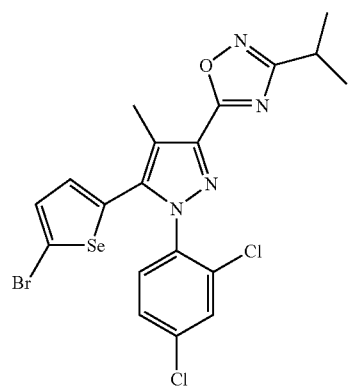

The compound was prepared in a manner similar to that described in Example 17. $^1$H NMR (CDCl$_3$, ppm) 7.49 (d, 1H), 7.40 (s, 1H), 7.38 (d, 1H), 7.19 (d, 1H), 6.90 (d, 1H), 3.20 (septet, 1H), 2.52 (s, 3H), 1.41 (d, 6H); ESMS 544.9 (M+1).

Example 19

Preparation of 5-(5-(5-bromothiophen-2-yl)-1-(2,4-dichlorophenyl)-4-methyl-1H-pyrazol-3-yl)-3-tert-butyl-1,2,4-oxadiazole

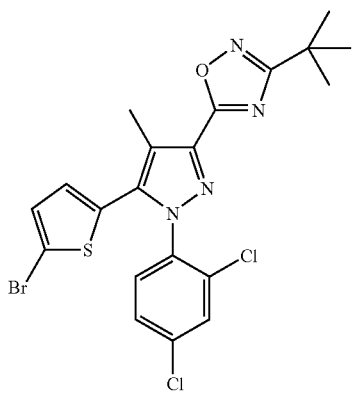

The compound was prepared in a manner similar to that described in Example 17. $^1$H NMR (CDCl$_3$, ppm) 7.48 (d, 1H), 7.40 (s, 1H), 7.37 (d, 1H), 6.97 (d, 1H), 6.70 (d, 1H), 2.52 (s, 3H), 1.45 (s, 9H); ESMS 511.1 (M+1).

Example 20

Preparation of 5-(5-(5-bromothiophen-2-yl)-1-(2,4-dichlorophenyl)-4-methyl-1H-pyrazol-3-yl)-3-isopropyl-1,2,4-oxadiazole

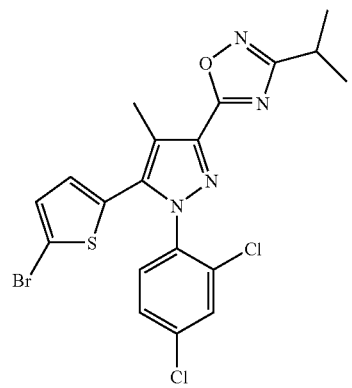

The compound was prepared in a manner similar to that described in Example 17. $^1$H NMR (CDCl$_3$, ppm) 7.49 (d, 1H), 7.40 (s, 1H), 7.37 (d, 1H), 6.98 (d, 1H), 6.69 (d, 1H), 3.21 (septet, 1H), 2.52 (s, 3H), 1.41 (d, 6H); ESMS 496.9 (M+1).

Example 21

Preparation of 5-(5-(5-bromothiophen-2-yl)-1-(2,4-dichlorophenyl)-4-methyl-1H-pyrazol-3-yl)-3-ethyl-1,2,4-oxadiazole

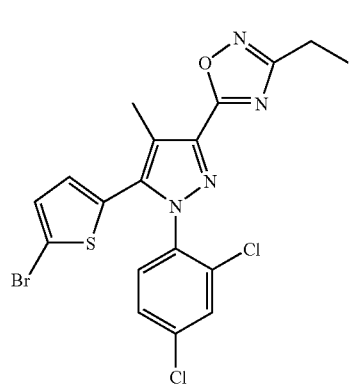

The compound was prepared in a manner similar to that described in Example 17. $^1$H NMR (CDCl$_3$, ppm) 7.49 (d, 1H), 7.39 (s, 1H), 7.37 (d, 1H), 6.98 (d, 1H), 6.69 (d, 1H), 2.86 (q, 2H), 2.52 (s, 3H), 1.40 (t, 3H); ESMS 482.9 (M+1).

Example 22

Preparation of (E)-3-tert-butyl-5-(1-(2,4-dichlorophenyl)-4-methyl-5-(5-(prop-1-enyl)thiophen-2-yl)-1H-pyrazol-3-yl)-1,2,4-oxadiazole

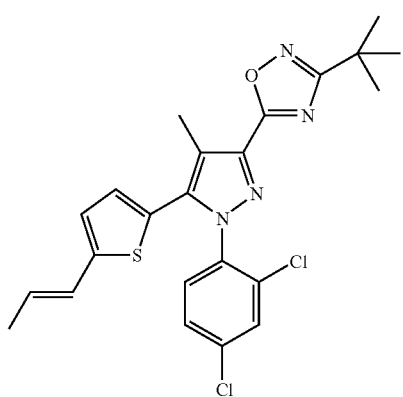

The compound was prepared in a manner similar to that described in Example 17. ¹H NMR (CDCl₃, ppm) 7.47 (d, 1H), 7.40 (s, 1H), 7.36 (d, 1H), 6.73-6.72 (m, 2H), 6.42 (d, 1H), 6.05 (dq, 1H), 2.54 (s, 3H), 1.84 (d, 3H), 1.45 (s, 9H); ESMS 473.0 (M+1).

Example 23

Preparation of (E)-5-(1-(2,4-dichlorophenyl)-4-methyl-5-(5-(prop-1-enyl)thiophen-2-yl)-1H-pyr-azol-3-yl)-3-isopropyl-1,2,4-oxadiazole

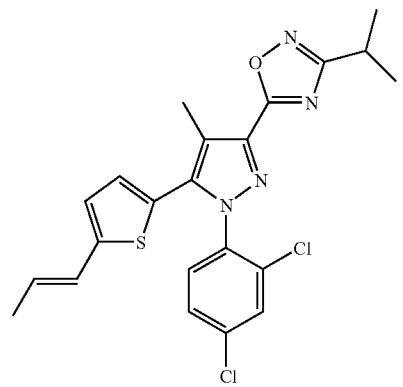

The compound was prepared in a manner similar to that described in Example 17. ¹H NMR (CDCl₃, ppm) 7.47 (d, 1H), 7.40 (s, 1H), 7.35 (d, 1H), 6.73-6.72 (m, 2H), 6.42 (d, 1H), 6.05 (dq, 1H), 3.20 (septet, 1H), 2.54 (s, 3H), 1.84 (d, 3H), 1.41 (d, 6H); ESMS 459.1 (M+1).

Example 24

Preparation of 3-tert-butyl-5-(1-(2,4-dichlorophenyl)-5-(5-(3,3-dimethylbut-1-ynyl)thiophen-2-yl)-4-methyl-1H-pyrazol-3-yl)-1,2,4-oxadiazole

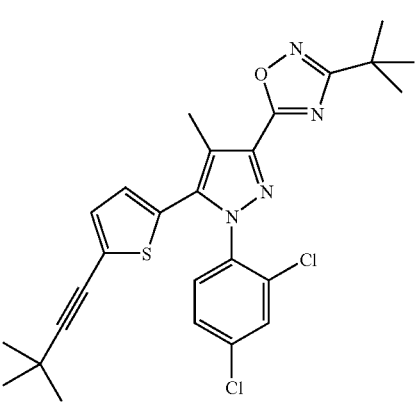

The compound was prepared in a manner similar to that described in Example 17. ¹H NMR (CDCl₃, ppm) 7.47 (d, 1H), 7.39 (s, 1H), 7.36 (d, 1H), 6.98 (d, 1H), 6.72 (d, 1H), 2.52 (s, 3H), 1.45 (s, 9H), 1.29 (s, 9H).

Example 25

Preparation of 5-(1-(2,4-dichlorophenyl)-5-(5-(3,3-dimethylbut-1-ynyl)thiophen-2-yl)-4-methyl-1H-pyrazol-3-yl)-3-isopropyl-1,2,4-oxadiazole

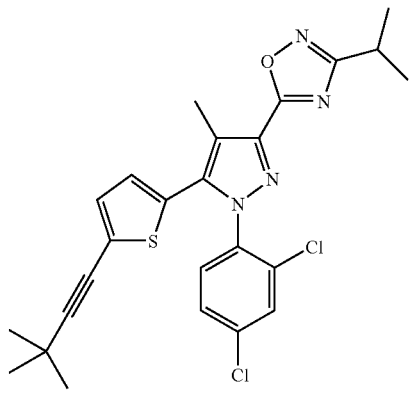

The compound was prepared in a manner similar to that described in Example 17. ¹H NMR (CDCl₃, ppm) 7.47 (d, 1H), 7.39 (s, 1H), 7.36 (d, 1H), 6.98 (d, 1H), 6.72 (d, 1H), 3.20 (septet, 1H), 2.53 (s, 3H), 1.41 (d, 6H), 1.29 (s, 9H); ESMS 499.2 (M+1).

Example 26

Preparation of 3-tert-butyl-5-(1-(2,4-dichlorophenyl)-5-(5-(hex-1-ynyl)thiophen-2-yl)-4-methyl-1H-pyrazol-3-yl)-1,2,4-oxadiazole

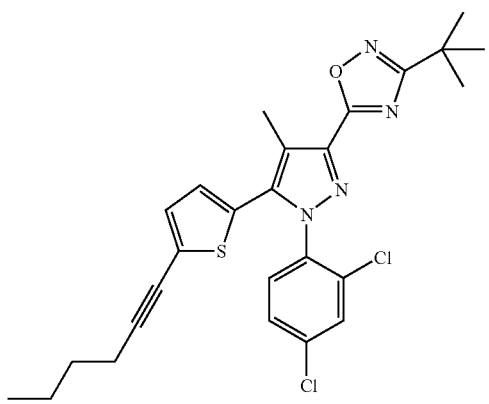

The compound was prepared in a manner similar to that described in Example 17. $^1$H NMR (CDCl$_3$, ppm) 7.47 (d, 1H), 7.40 (s, 1H), 7.36 (d, 1H), 7.19 (d, 1H), 6.99 (d, 1H), 6.75 (d, 1H), 2.54 (s, 3H), 2.41 (t, 2H), 1.61-1.38 (m, 4H), 1.45 (s, 9H), 0.92 (t, 3H); ESMS 513.1 (M+1).

Example 27

Preparation of 5-(1-(2,4-dichlorophenyl)-5-(5-(hex-1-ynyl)thiophen-2-yl)-4-methyl-1H-pyrazol-3-yl)-3-isopropyl-1,2,4-oxadiazole

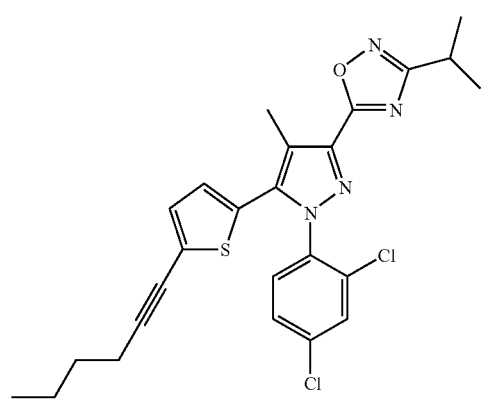

The compound was prepared in a manner similar to that described in Example 17. $^1$H NMR (CDCl$_3$, ppm) 7.47 (d, 1H), 7.40 (s, 1H), 7.36 (d, 1H), 6.99 (d, 1H), 6.75 (d, 1H), 3.20 (septet, 1H), 2.54 (s, 3H), 2.41 (t, 2H), 1.61-1.37 (m, 4H), 1.41 (d, 6H), 0.92 (t, 3H); ESMS 499.1 (M+1).

Example 28

Preparation of 5-(1-(2,4-dichlorophenyl)-5-(5-(hex-1-ynyl)thiophen-2-yl)-4-methyl-1H-pyrazol-3-yl)-3-ethyl-1,2,4-oxadiazole

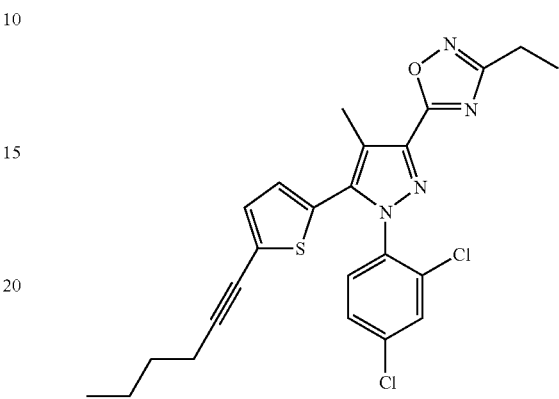

The compound was prepared in a manner similar to that described in Example 17. $^1$H NMR (CDCl$_3$, ppm) 7.48 (d, 1H), 7.40 (s, 1H), 7.36 (d, 1H), 6.99 (d, 1H), 6.75 (d, 1H), 2.86 (q, 2H), 2.54 (s, 3H), 2.41 (t, 2H), 1.62-1.41 (m, 4H), 1.39 (t, 3H), 0.93 (t, 3H); ESMS 485.1 (M+1).

Example 29

Preparation of 3-tert-butyl-5-(1-(2,4-dichlorophenyl)-4-methyl-5-(5-(pent-1-ynyl)thiophen-2-yl)-1H-pyrazol-3-yl)-1,2,4-oxadiazole

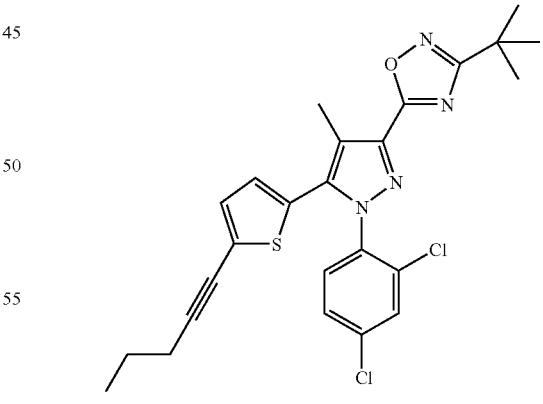

The compound was prepared in a manner similar to that described in Example 17. $^1$H NMR (CDCl$_3$, ppm) 7.47 (d, 1H), 7.40 (s, 1H), 7.36 (d, 1H), 6.99 (d, 1H), 6.75 (d, 1H), 2.54 (s, 3H), 2.39 (t, 2H), 1.60 (sextet, 2H), 1.45 (s, 9H), 1.01 (t, 3H); ESMS 499.1 (M+1).

Example 30

Preparation of 5-(1-(2,4-dichlorophenyl)-4-methyl-5-(5-(pent-1-ynyl)thiophen-2-yl)-1H-pyrazol-3-yl)-3-isopropyl-1,2,4-oxadiazole

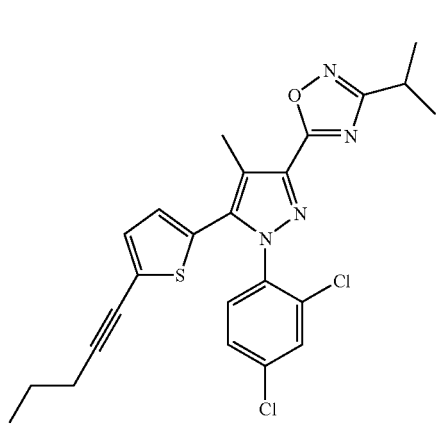

The compound was prepared in a manner similar to that described in Example 17. $^1$H NMR (CDCl$_3$, ppm) 7.48 (d, 1H), 7.40 (s, 1H), 7.36 (d, 1H), 7.00 (d, 1H), 6.75 (d, 1H), 3.20 (septet, 1H), 2.54 (s, 3H), 2.39 (t, 2H), 1.61 (sextet, 2H), 1.41 (d, 6H), 1.02 (t, 3H); ESMS 485.1 (M+1).

Example 31

Preparation of 5-(1-(2,4-dichlorophenyl)-4-methyl-5-(5-(pent-1-ynyl)thiophen-2-yl)-1H-pyrazol-3-yl)-3-ethyl-1,2,4-oxadiazole

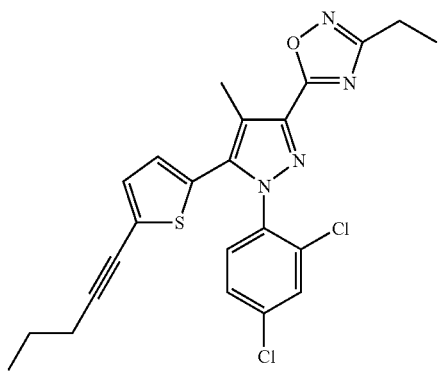

The compound was prepared in a manner similar to that described in Example 17. $^1$H NMR (CDCl$_3$, ppm) 7.48 (d, 1H), 7.40 (s, 1H), 7.36 (d, 1H), 7.00 (d, 1H), 6.75 (d, 1H), 2.86 (q, 2H), 2.54 (s, 3H), 2.39 (t, 2H), 1.61 (sextet, 2H), 1.40 (t, 3H), 1.02 (t, 3H); ESMS 471.1 (M+1).

Example 32

Preparation of 3-tert-butyl-5-(5-(5-(cyclopentylethynyl)thiophen-2-yl)-1-(2,4-dichlorophenyl)-4-methyl-1H-pyrazol-3-yl)-1,2,4-oxadiazole

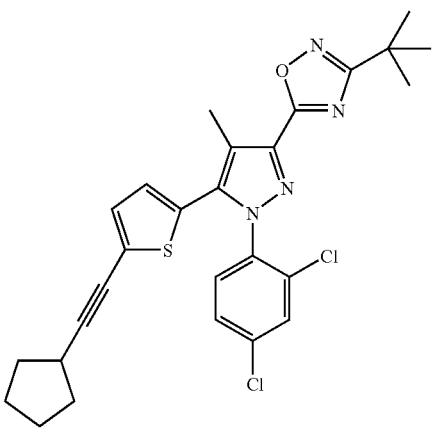

The compound was prepared in a manner similar to that described in Example 17. $^1$H NMR (CDCl$_3$, ppm) 7.47 (d, 1H), 7.40 (s, 1H), 7.36 (d, 1H), 6.98 (d, 1H), 6.74 (d, 1H), 2.81 (quintet, 1H), 2.53 (s, 3H), 2.01-1.55 (m, 8H), 1.45 (s, 9H); ESMS 525.1 (M+1).

Example 33

Preparation of 5-(5-(5-(cyclopentylethynyl)thiophen-2-yl)-1-(2,4-dichlorophenyl)-4-methyl-1H-pyrazol-3-yl)-3-isopropyl-1,2,4-oxadiazole

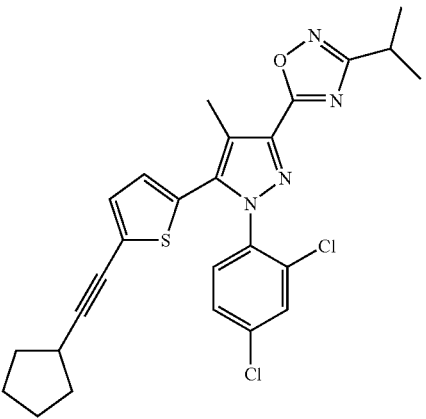

The compound was prepared in a manner similar to that described in Example 17. $^1$H NMR (CDCl$_3$, ppm) 7.47 (d, 1H), 7.39 (s, 1H), 7.36 (d, 1H), 6.98 (d, 1H), 6.74 (d, 1H), 3.20 (septet, 1H), 2.82 (quintet, 1H), 2.54 (s, 3H), 2.01-1.53 (m, 8H), 1.41 (d, 6H).

Example 34

Preparation of 5-(5-(5-(cyclopentylethynyl)thiophen-2-yl)-1-(2,4-dichlorophenyl)-4-methyl-1H-pyrazol-3-yl)-3-ethyl-1,2,4-oxadiazole

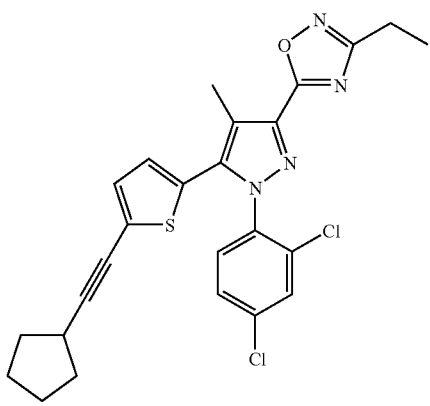

The compound was prepared in a manner similar to that described in Example 17. $^1$H NMR (CDCl$_3$, ppm) 7.47 (d, 1H), 7.40 (s, 1H), 7.36 (d, 1H), 6.98 (d, 1H), 6.74 (d, 1H), 2.86 (q, 2H), 2.82 (quintet, 1H), 2.01-1.56 (m, 8H), 1.39 (t, 3H); ESMS 497.1 (M+1).

Example 35

Biological Assays

Human CB1 and CB2 receptors were obtained from HEK293 cell lines stably expressing CB1 and CB2 receptors. Briefly, cells expressing a CB1 or CB2 receptor were harvested and subjected to sonication. The lyzed cells were centrifuged for 30 minutes at 43,000×g at 4° C. The resultant pellets were re-suspended in a buffer (50 mM Tris, 5 mM MgCl$_2$, 2.5 mM EDTA, pH 7.4, 10% sucrose) and stored at −80° C. The protein concentration of the purified membrane was determined by the Bradford method as described in the manual provided by Bio-Rad Laboratories, Inc. (Hercules, Calif.).

The affinity of compounds 1-18 to a CB1 or CB2 receptor was determined by in vitro competitive binding assays as follows. 0.2~8 μg of membrane fractions prepared from cell lines expressing a human CB1 or CB2 receptor according to the method described above were added to 0.75 nM [$^3$H]CP55,940 (a ligand that specifically binds to CB1 and CB2 receptors) and a test compound in a buffer (pH 7.4) containing 50 mM Tris-HCl, 5 mM MgCl$_2$, 1 mM EDTA, and 0.3% BSA. Non-labeled CP55,940 (1 μM) was used instead of the test compound in a control assay. The mixture was incubated for 1.5 hours at 30° C. in Multiscreen microplates (Millipore, Billerica, Mass.) to allow the test compound or [$^3$H]CP55,940 to bind to the receptor. At the end of the incubation period, the binding reaction was terminated by Manifold filtration, in which the membrane fractions (containing a CB1 or CB2 receptor) were retained on the filters. The filters were then washed with ice-cold wash buffer (50 mM Tris, pH 7.4, 0.25% BSA) four times to remove free [$^3$H]CP55,940. The radioactivity bound to the filters was measured by Topcount (Perkin Elmer Inc.). IC$_{50}$ (the concentration of the test compound required to inhibit 50% of the binding of [$^3$H]CP55,940 to the receptor) were calculated.

The activity of each test compound in modulating a CB1 receptor was determined by the method described in the following paragraph using the DELFIA GTP-binding kit supplied by Perkin Elmer Inc. (Boston, Mass.). The DELFIA GTP-binding assay is a time-resolved fluorometric assay based on GDP-GTP exchange on G-protein subunits after activation of a G protein-coupled receptor. Note that stimulation of a CB1 receptor by CP55,940 results in replacement of GDP by GTP on the α-subunit of G-protein, leading to GTP-Gα complex, i.e., the activated form of G-protein. Eu-GTP, a non-hydrolysable GTP labeled with the Europium chelate, is used to monitor agonist-dependent activation of G-protein. See Peltonen et al., Eur. J. Pharmacol. (1998) 355:275.

Plasma membrane derived from HEK293 cells expressing a human CB1 receptor was suspended in an assay buffer (50 mM HEPES, pH 7.4, 100 mM NaCl, 100 μg/mL saponin, 5 mM MgCl$_2$, 2 μM GDP, 0.5% BSA). An aliquot of the membrane was added to each well of AcroPlate (Pall Life Sciences, Ann Arbor, Mich.) together with a test compound (various concentrations in 0.1% DMSO) and CP55,940 (20 nM in the assay buffer). The assay plate was incubated in dark at 30° C. for 60 minutes. Eu-GTP was then added to each well and the plate was incubated for another 30 minutes at 30° C. in dark. The plate was washed four times with a wash solution provided in the assay kit. Binding of Eu-GTP was detected based on the fluorescence signal determined by a Victor 2 multi-label reader. The EC$_{50}$ value (i.e., 50% inhibition of CP55,940-stimulating Eu-GTP binding) for each test compound was determined by a concentration-response curve using nonlinear regression (Prism; GraphPad, San Diego, Calif.).

All of the test compounds had IC$_{50}$ values between 1 nM and 10 μM for inhibiting binding of [$^3$H]CP55,940 to CB1 and CB2 receptors in the competitive binding assay and had EC$_{50}$ values between 1 nM and 10 μM for inhibiting Eu-GTP binding by modulating CP55,940-stimulating CB1 receptor activation in the DELFIA GTP-binding kit assay.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to oxadiazole compounds described above also can be made, screened for the above-described activities and used to practice this invention. Thus, other embodiments are also within the claims.

What is claimed is:

1. A compound of formula (I):

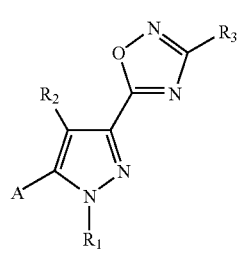

wherein
- each of $R_1$, $R_2$, and $R_3$, independently, is H, halo, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, or heteroaryl; and
- A is heteroaryl optionally substituted with halo, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, or heteroaryl or optionally fused with a 3-8 membered ring containing 0-3 heteroatoms.

2. The compound of claim 1, wherein $R_1$ is aryl substituted with halo.

3. The compound of claim 2, wherein $R_1$ is 2,4-dichlorophenyl.

4. The compound of claim 1, wherein $R_3$ is $C_1$-$C_{10}$ alkyl.

5. The compound of claim 1, wherein A is 5-membered heteroaryl optionally substituted with halo, $C_1$-$C_{10}$ alkyl, $C_2$-$C_{10}$ alkenyl, or $C_2$-$C_{10}$ alkynyl or optionally fused with a 3-8 membered ring containing 0-3 heteroatoms.

6. The compound of claim 5, wherein A is thienyl substituted with halo, $C_1$-$C_{10}$ alkyl, $C_2$-$C_{10}$ alkenyl, or $C_2$-$C_{10}$ alkynyl.

7. The compound of claim 6, wherein A is thien-2-yl substituted with Br, $C_1$-$C_{10}$ alkyl, $C_2$-$C_{10}$ alkenyl, or $C_2$-$C_{10}$ alkynyl.

8. The compound of claim 7, wherein $R_1$ is aryl substituted with halo and $R_3$ is $C_1$-$C_{10}$ alkyl.

9. The compound of claim 5, wherein A is thien-2-yl fused with a 5-7 membered ring containing 0-1 nitrogen atom.

10. The compound of claim 9, wherein $R_1$ is aryl substituted with halo and $R_3$ is $C_1$-$C_{10}$ alkyl.

11. The compound of claim 5, wherein A is selenophenyl substituted with halo, $C_1$-$C_{10}$ alkyl, $C_2$-$C_{10}$ alkenyl, or $C_2$-$C_{10}$ alkynyl.

12. The compound of claim 11, wherein A is selenophen-2-yl substituted with Br, $C_1$-$C_{10}$ alkyl, $C_2$-$C_{10}$ alkenyl, or $C_2$-$C_{10}$ alkynyl.

13. The compound of claim 12 wherein A is selenophen-2-yl substituted with Br.

14. The compound of claim 13, wherein $R_1$ is aryl substituted with halo and $R_3$ is $C_1$-$C_{10}$ alkyl.

15. The compound of claim 5, wherein A is selenophenyl fused with a 3-8 membered ring containing 0-3 heteroatoms.

16. The compound of claim 15, wherein A is selenophen-2-yl fused with a 5-7 membered ring containing 0 or 1 nitrogen atom.

17. The compound of claim 16, wherein $R_1$ is aryl substituted with halo and $R_3$ is $C_1$-$C_{10}$ alkyl.

18. The compound of claim 1, wherein the compound is selected from

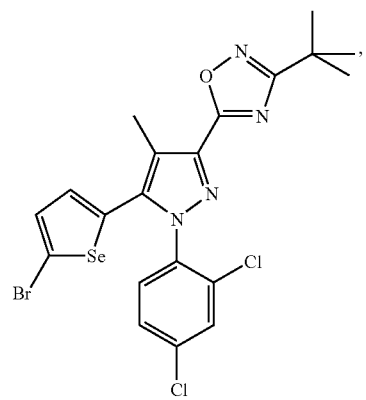

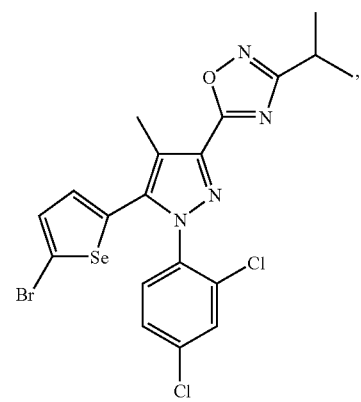

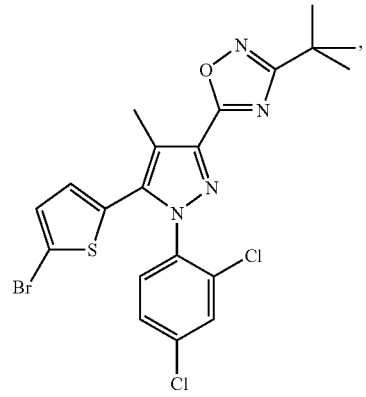

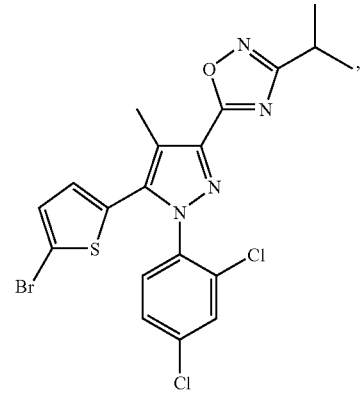

-continued
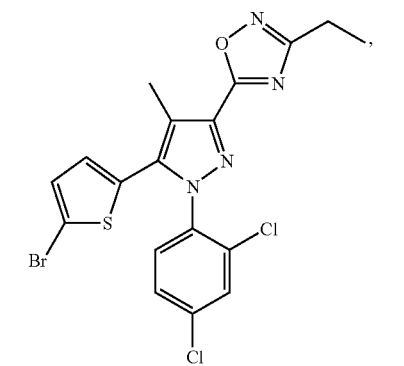
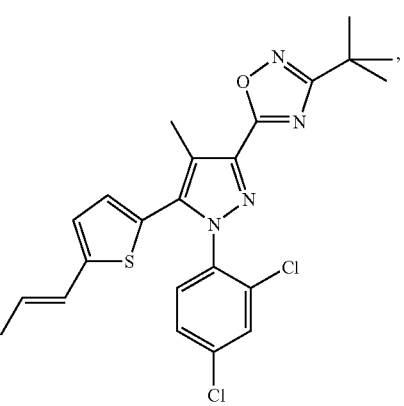
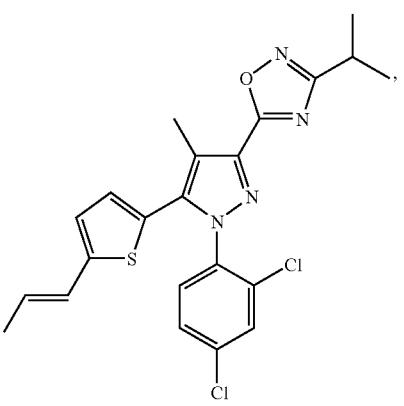
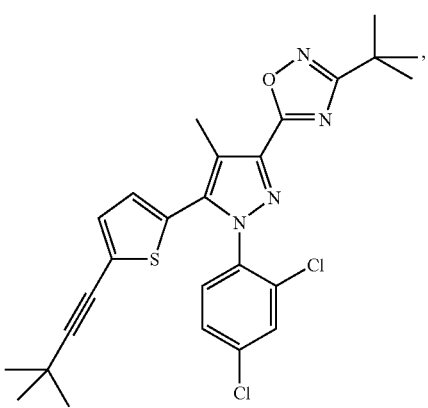
-continued
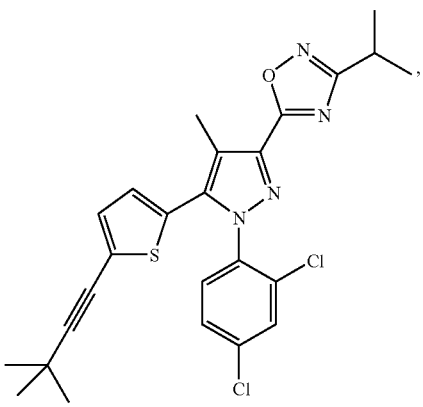
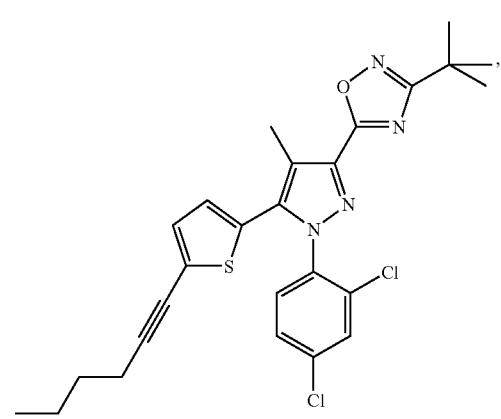
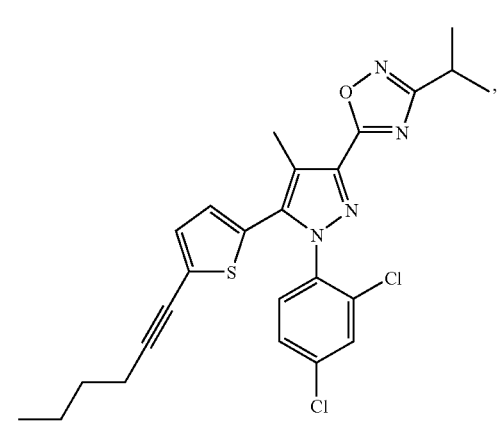
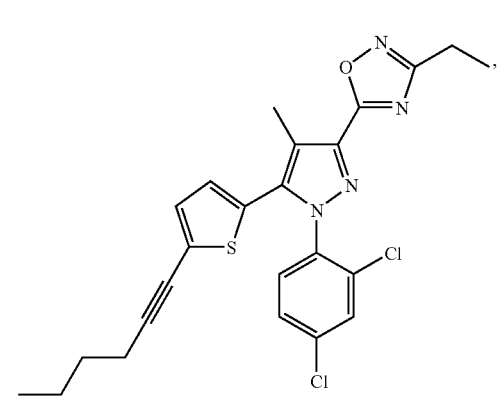

-continued

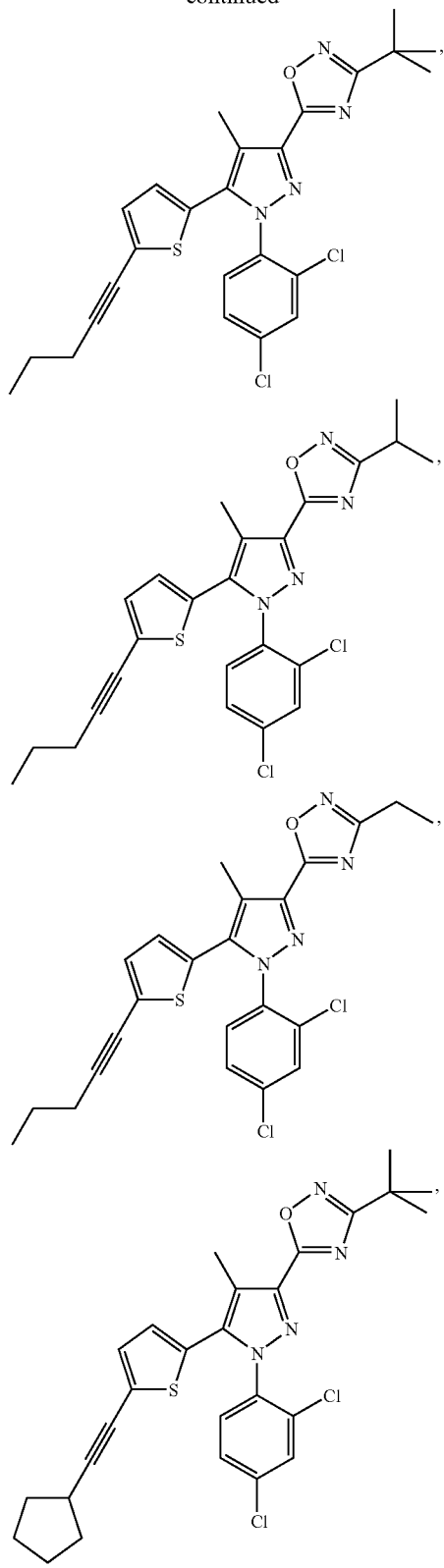

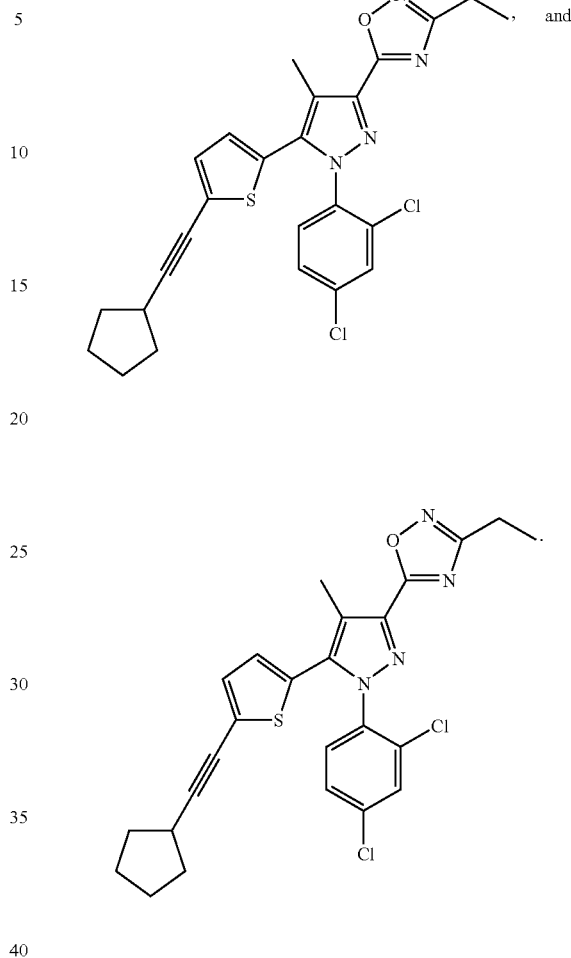

19. A pharmaceutical composition, comprising a compound of claim 1 and a pharmaceutically acceptable carrier.

20. A method for treating a cannabinoid receptor-mediated disorder, comprising administering to a subject in need thereof an effective amount of a compound of claim 1, wherein the cannabinoid receptor-mediated disorder is metabolic syndrome, obesity, hyperlipidemia, type II diabetes, atherosclerosis, substance addiction, liver cirrhosis, schizophrenia, sexual dysfunction, anxiety, depression, motivational deficiency syndrome, learning or memory dysfunction, analgesia, haemorrhagic shock, ischemia, neuropathic pain, antiemesis, hair loss, high intraocular pressure, bronchodilation or osteoporosis.

21. The method of claim 20, wherein the cannabinoid receptor-mediated disorder is metabolic syndrome, obesity, hyperlipidemia, type II diabetes, atherosclerosis, substance addiction, liver cirrhosis, schizophrenia, or sexual dysfunction.

* * * * *